United States Patent [19]

Lüthy

[11] Patent Number: 4,943,583

[45] Date of Patent: Jul. 24, 1990

[54] HETEROCYCLIC COMPOUNDS

[75] Inventor: Christoph Lüthy, Schwerzenbach, Switzerland

[73] Assignee: Hoffmann-La Roche Inc., Nutley, N.J.

[21] Appl. No.: 126,804

[22] Filed: Dec. 1, 1987

[30] Foreign Application Priority Data

Dec. 1, 1986 [CH]  Switzerland .......................... 4785/86
Sep. 16, 1987 [CH]  Switzerland .......................... 3571/87

[51] Int. Cl.$^5$ ................... C07D 271/113; A01N 43/82
[52] U.S. Cl. ..................................... 514/364; 546/277; 548/144; 548/136; 548/263.2; 514/340
[58] Field of Search ......................... 548/144; 546/277; 514/364, 340

[56]  References Cited

PUBLICATIONS

Petrova, Zh Org Khim 22 1297 (1986).

*Primary Examiner*—Robert Gerstl

*Attorney, Agent, or Firm*—George M. Gould; William H. Epstein; Dennis P. Tramaloni

[57]  ABSTRACT

The invention is concerned with novel compounds of the formula

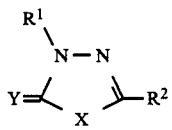

wherein $R^1$ signifies optionally substituted phenyl or pyridyl, $R^2$ signifies substituted phenyl, X signifies oxygen, sulfur or $NR^3$, Y signifies oxygen or sulfur and $R^3$ signifies methyl, halomethyl or 2-propynyl, and their manufacture, pest control compositions which contain said compounds as the active ingredient and the use of the active substances or compositions for the control of pests.

9 Claims, No Drawings

HETEROCYCLIC COMPOUNDS

BRIEF SUMMARY OF THE INVENTION

The invention is concerned with novel compounds of the formula

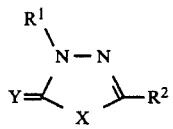

wherein $R^1$ signifies optionally substituted phenyl or pyridyl, $R^2$ signifies substituted phenyl, X signifies oxygen, sulfur or $NR^3$, Y signifies oxygen or sulfur and $R^3$ signifies methyl, halomethyl or 2-propynyl.

These compounds have been found to be useful in pest control compositions and are especially suitable as an active ingredient for the control of insects and mites.

DETAILED DESCRIPTION OF THE INVENTION

The present invention is concerned with heterocyclic compounds, namely 1,3,4-oxadiazol-2(3H)-ones and -thiones, 1,3,4-thiadiazol-2(3H)-ones and -thiones and 2,4-dihydro-3H-1,2,4-triazol-3-ones and -thiones of the general formula

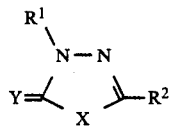

wherein
- $R^1$ signifies phenyl optionally substituted with up to 4 halogen atoms, 1 to 3 $C_{1-4}$-alkyl groups, 1 or 2 halomethyl groups, a $C_{1-3}$-alkoxy group, a $C_{1-2}$-alkylthio group, a $C_{1-3}$-haloalkoxy group, a $C_{1-2}$-haloalkylthio group and/or a cyano group or pyridyl optionally substituted with 1 or 2 halogen atoms, 1 or 2 methyl groups or a halomethyl group,
- $R^2$ signifies phenyl substituted with up to 3 halogen atoms, a methyl group, a halomethyl group and/or 1 or 2 methoxy groups, with at least one of the two o-positions being occupied,
- X signifies oxygen, sulfur or $NR^3$,
- Y signifies oxygen or sulfur, and
- $R^3$ signifies methyl, halomethyl or 2-propynyl.

The compounds of formula I are pest control agents and are especially suitable for the control of insects and mites, e.g. spider mites. Accordingly, the invention also embraces pest control compositions which contain compounds of formula I as the active substance, a process for the manufacture of these compounds as well as the use of these compounds or compositions for the control of pests.

The term "halogen" used in the above definition of the compounds of formula I embraces fluorine, chlorine, bromine and iodine. The "halomethyl", "$C_{1-3}$-haloalkoxy" and "$C_{1-2}$-haloalkylthio" groups can in each case have one or more (similar or different) halogen substituents. The substituents in the substituted phenyl group $R^1$ or $R^2$ as well as in the case of $R^1$=substituted pyridyl can also be the same or different. Those alkyl, alkoxy or haloalkoxy groups which contain 3 or 4 carbon atoms can be straight-chain or branched.

If $R^1$ signifies phenyl substituted with up to 4 halogen atoms, this has especially 1 to 4 fluorine atoms, 1 to 3 chlorine atoms, a bromine atom and/or an iodine atom. On the other hand, if $R^1$ signifies pyridyl substituted with 1 or 2 halogen atoms, this has especially 1 or 2 fluorine atoms, 1 or 2 chlorine atoms or a bromine atom. In the case of $R^2$, which can signify phenyl substituted with up to 3 halogen atoms, there are present as substituents especially 1 to 3 fluorine atoms, 1 or 2 chlorine atoms, a bromine atom and/or an iodine atom.

$R^1$ preferably signifies a mono- or disubstituted phenyl group in which the substituent(s) is/are one or two fluorine atoms, one or two chlorine atoms, a bromine atom, one or two methyl groups, a trifluoromethyl group and/or a halomethoxy group and one o-position is occupied. Especially preferred in this case are fluorine, chlorine, bromine, methyl or trifluoromethyl.

Independently of the significance of $R^1$, $R^2$ preferably signifies a mono- or disubstituted phenyl group in which the substituent(s) is/are one or two fluorine atoms, one or two chlorine atoms and/or a bromine atom. Especially preferably, $R^2$ signifies 2-chlorophenyl, 2-chloro-4-fluorophenyl, 2-chloro-6-fluorophenyl or 2,6-difluorophenyl.

X preferably stands for oxygen.

Preferred individual compounds of formula I are:
5-(2-Chloro-6-fluorophenyl)-3-(α,α,α-trifluoro-o-tolyl)-1,3,4-oxadiazol-2(3H)-one,
5-(2-chloro-6-fluorophenyl)-3-(2-chlorophenyl)-1,3,4-oxadiazol-2(3H)-on,
5-(2,6-difluorophenyl)-3-(α,α,α-trifluoro-o-tolyl)-1,3,4-oxadiazol-2(3H)-one,
5-(2-chloro-4-fluorophenyl)-3-(2-chlorophenyl)-1,3,4-oxadiazol-2(3H)-one,
5-(2-chloro-6-fluorophenyl)-3-(3-chloro-o-tolyl)-1,3,4-oxadiazol-2(3H)-one,
5-(2-chloro-6-fluorophenyl)-3-(2-chlorophenyl)-1,3,4-oxadiazole-2(3H)-thione,
3-(2-chlorophenyl)-5-(2,6-difluorophenyl)-1,3,4-oxadiazol-2(3H)-one,
3-(2-chlorophenyl)-5-(2,6-dichlorphenyl)-1,3,4-oxadiazol-2(3H)-one,
5-(2-chlorophenyl)-3-(α,α,α-trifluoro-o-tolyl)-1,3,4-oxadiazol-2(3H)-one,
5-(2,6-difluorophenyl)-3-(α,α,α-trifluoro-o-tolyl)-1,3,4-oxadiazole-2(3H)-thione,
3-(2-bromophenyl)-5-(2,6-difluorophenyl)-1,3,4-oxadiazol-2(3H)-one and
5-(2-chloro-6-fluorophenyl)-3-(2-fluorophenyl)-1,3,4-oxadiazol-2(3H)-one.

Further representatives of compounds of formula I are:
5-(2-Chlorophenyl)-3-(2-fluorophenyl)-1,3,4-oxadiazol-2(3H)-one,
3-(2,4-dichlorophenyl)-5-(2,6-difluorophenyl)-1,3,4-oxadiazol-2(3H)-one,
3-(2-chloro-4-fluorophenyl)-5-(2-chloro-6-fluorophenyl)-1,3,4-oxadiazol-2(3H)-one,
5-(2,4-difluorophenyl)-3-(α,α,α-trifluoro-o-tolyl)-1,3,4-oxadiazol-2(3H)-one,
5-(2-chloro-6-fluorophenyl)-3-(2-chloro-4-trifluoromethyl-phenyl)-1,3,4-oxadiazol-2(3H)-one,
3-(3,5-dichloro-2,4-difluorophenyl)-5-(2,6-difluorophenyl)-1,3,4-oxadiazol-2(3H)-one,
3-(2-chlorophenyl)-5-(2-fluorophenyl)-1,3,4-oxadiazol-2(3H)-one, 5-(2-bromophenyl)-3-(2-chlorophenyl)-1,3,4-oxadiazol-2(3H)-one,
3-(3-chloro-o-tolyl)-5-(2,6-difluorophenyl)-1,3,4-oxadiazol-2(3H)-one,
3-(2,5-dichloro-3-trifluoromethyl-phenyl)-5-(2,6-difluoro-phenyl)-1,3,4-oxadiazol-2(3H)-one,
5-(2-chloro-6-fluorophenyl)-3-(2-trifluoromethoxy-phenyl)-1,3,4-oxadiazol-2(3H)-one,
5-(2-chloro-4-fluorophenyl)-3-(2-methoxy-m-tolyl)-1,3,4-oxadiazol-2(3H)-one,
3-(2-ethoxy-m-tolyl)-5-(2-chlorophenyl)-1,3,4-oxadiazol-2(3H)-one,
3-(2-ethoxy-3-ethylphenyl)-5-(2,6-difluorophenyl)-1,3,4-oxadiazol-2(3H)-one,
5-(2-chlorophenyl)-3-(2-isopropoxy-m-tolyl)-1,3,4-oxadiazol-2(3H)-one,
5-(2-chloro-6-fluorophenyl)-3-(2-methoxy-p-tolyl)-1,3,4-oxadiazol-2(3H)-one,
5-(2-chlorophenyl)-3-(4-fluoro-2-methoxyphenyl)-1,3,4-oxadiazol-2(3H)-one,
5-(2-chlorophenyl)-3-(4-trifluoromethoxy-phenyl)-1,3,4-oxadiazol-2(3H)-one,
3-[3,5-dichloro-4-(1,1,2,2-tetrafluoroethoxy)-phenyl]-5-(2,6-difluorophenyl)-1,3,4-oxadiazol-2(3H)-one,
5-(2-chlorophenyl)-3-[2,5-dichloro-4-(1,1,2,3,3,3-hexafluoropropoxy)-phenyl]-1,3,4-oxadiazol-2(3H)-one,
5-(2-chloro-6-fluorophenyl)-3-(2-chloro-5-trifluoromethyl-phenyl)-1,3,4-oxadiazol-2(3H)-one,
5-(2,6-difluorophenyl)-3-(α,α,α-trifluoro-p-tolyl)-1,3,4-oxadiazol-2(3H)-one,
3-(2-chlorophenyl)-5-(2-chloro-4,6-difluorophenyl)-1,3,4-oxadiazol-2(3H)-one,
5-(2-chloro-6-fluorophenyl)-3-(o-tolyl)-1,3,4-oxadiazol-2(3H)-one,
3-(3-chloro-2-trifluoromethyl-phenyl)-5-(2,6-difluorophenyl)-1,3,4-oxadiazol-2(3H)-one,
3-(2-cyanophenyl)-5-(2,6-difluorophenyl)-1,3,4-oxadiazol-2(3H)-one,
3-(2-chlorophenyl)-5-(2-chloro-5-fluorophenyl)-1,3,4-oxadiazol-2(3H)-one,
5-(3-chloro-2,4-difluorophenyl)-5-(2-chlorophenyl)-1,3,4-oxadiazol-2(3H)-one,
3-(3-chloro-4-trifluoromethyl-phenyl)-5-(2,6-difluorophenyl)-1,3,4-oxadiazol-2(3H)-one,
3-(3,5-dichloro-o-tolyl)-5-(2,6-difluorophenyl)-1,3,4-oxadiazol-2(3H)-one,
3-(2,3-dichlorophenyl)-5-(2,6-difluorophenyl)-1,3,4-oxadiazol-2(3H)-one,
3-(3-chloro-2-pyridyl)-5-(2,6-difluorophenyl)-1,3,4-oxadiazol-2(3H)-one,
5-(2-chloro-6-fluorophenyl)-3-(α,α,α-trifluoro-o-tolyl)-1,3,4-oxadiazole-2(3H)-thione,
5-(2-chloro-4-fluorophenyl)-3-(α,α,α-trifluoro-o-tolyl)-1,3,4-oxadiazole-2(3H)-thione,
5-(2,6-difluorophenyl)-3-(2-methoxy-m-tolyl)-1,3,4-oxadiazole-2(3H)-thione,
5-(2-chloro-6-fluorophenyl)-3-(3-chloro-o-tolyl)-1,3,4-oxadiazole-2(3H)-thione,
5-(2-chloro-6-fluorophenyl)-2-(2,3-dichlorophenyl)-4-methyl-2,4-dihydro-3H-1,2,4-triazol-3-one,
5-(2-chlorophenyl)-4-methyl-2-(2,6-dichloro-4-pyridyl)-2,4-dihydro-3H-1,2,4-triazol-3-one,
4-difluoromethyl-5-(2,6-difluorophenyl)-2-(α,α,α-trifluoro-o-tolyl)-2,4-dihydro-3H-1,2,4-triazol-3-one,
2-(2-chlorophenyl)-5-(2-chloro-6-fluorophenyl)-4-difluoromethyl-2,4-dihydro-3H-1,2,4-triazol-3-one,
2-(2-chlorophenyl)-4-difluoromethyl-5-(2,6-difluorophenyl)-2,4-dihydro-3H-1,2,4-triazol-3-one,
5-(2-chloro-4-fluorophenyl)-4-difluoromethyl-2-(α,α,α-trifluoro-o-tolyl)-2,4-dihydro-3H-1,2,4-triazol-3-one,
2-(3-chloro-o-tolyl)-5-(2,6-difluorophenyl)-4-methyl-2,4-dihydro-3H-1,2,4-triazol-3-one,
2-(2-bromophenyl)-5-(2,6-difluorophenyl)-4-methyl-2,4-dihydro-3H-1,2,4-triazol-3-one,
2-(2-bromophenyl)-5-(2-chloro-6-fluorophenyl)-4-methyl-2,4-dihydro-3H-1,2,4-triazol-3-one,
5-(2-chloro-4-fluorophenyl)-4-methyl-2-(α,α,α-trifluoro-o-tolyl)-2,4-dihydro-3H-1,2,4-triazol-3-one,
5-(2,6-difluorophenyl)-4-methyl-2-(α,α,α-trifluoro-o-tolyl)-2,4-dihydro-3H-1,2,4-triazole-3-thione,
3-(2-chlorophenyl)-5-(2,4-dichlorophenyl)-1,3,4-oxadiazol-2(3H)-one,
5-(2-chloro-4-fluorophenyl)-3-(2,6-difluorophenyl)-1,3,4-oxadiazol-2(3H)-one,
3-(2-chloro-5-trifluoromethyl-phenyl)-5-(2,6-difluorophenyl)-1,3,4-oxadiazol-2(3H)-one,
2-(3,4-dichlorophenyl)-5-(2,6-difluorophenyl)-4-methyl-2,4-dihydro-3H-1,2,4-triazol-3-one,
5-(2,6-difluorophenyl)-3-(2-trifluoromethoxy-phenyl)-1,3,4-oxadiazol-2(3H)-one,
5-(2-chloro-6-fluorophenyl)-3-(2-difluoromethoxy-phenyl)-1,3,4-oxadiazol-2(3H)-one,
3-[2,5-dichloro-4-(1,1,2,2-tetrafluoroethoxy)-phenyl]-5-(2,6-difluorophenyl)-1,3,4-oxadiazol-2(3H)-one,
5-(2,6-difluorophenyl)-3-[4-(1,1,2,2-tetrafluoroethoxy)-3-trifluormethyl-phenyl]-1,3,4-oxadiazol-2(3H)-one,
5-(2-chloro-6-fluorophenyl)-3-(4-trifluoromethoxy-3-trifluoromethyl-phenyl)-1,3,4-oxadiazol-2(3H)-one,
3-[4-(2-chloro-1,1,2-trifluoroethoxy)-3,5-dichloro-phenyl]-5-(2,6-difluorophenyl)-1,3,4-oxadiazol-2(3H)-one,
3-[3,5-dichloro-4-(1,1,2,3,3,3-hexafluoropropoxy)-phenyl]-5-(2,6-difluorophenyl)-1,3,4-oxadiazol-2(3H)-one,
5-(2-chloro-6-fluorophenyl)-3-(2-chloro-4-trifluoromethylthio-phenyl)-1,3,4-oxadiazol-2(3H)-one,
5-(2-methoxyphenyl)-3-(α,α,α-trifluoro-o-tolyl)-1,3,4-oxadiazol-2(3)-one,
3-(4-chloro-3,5-difluorophenyl)-5-(2-chloro-6-fluorophenyl)-1,3,4-oxadiazol-2(3H)-one,
3-(2,4-difluorophenyl)-5-(2,6-difluorophenyl)-1,3,4-oxadiazol-2(3H)-one,
5-(2,6-difluorophenyl)-3-(2,3,4-trichlorophenyl)-1,3,4-oxadiazol-2(3H)-one,
3-(4-bromo-2-fluoro-5-trifluoromethyl-phenyl)-5-(2,6-difluorophenyl)-1,3,4-oxadiazol-2(3H)-one,
5-(2,6-difluorophenyl)-3-(4-fluoro-3-trifluoromethyl-phenyl)-1,3,4-oxadiazol-2(3H)-one,
3-(2-bromo-4-trifluoromethyl-phenyl)-5-(2,6-difluorophenyl)-1,3,4-oxadiazol-2(3H)-one,
5-(2-chloro-6-fluorophenyl)-3-(2-fluoro-5-trifluoromethyl-phenyl)-1,3,4-oxadiazol-2(3H)-one,
5-(2-chlorophenyl)-3-(2,6-difluoro-4-trifluoromethyl-phenyl)-1,3,4-oxadiazol-2(3H)-one,
5-(2,4,6-trifluorophenyl)-3-(α,α,α-trifluoro-o-tolyl)-1,3,4-oxadiazol-2(3H)-one,
5-(2-chloro-6-fluorophenyl)-3-(2-difluoromethyl-phenyl)-1,3,4-oxadiazol-2(3H)-one,
5-(2-chloro-4-fluorophenyl)-3-(5-chloro-2,3,4-trifluoro-phenyl)-1,3,4-oxadiazol-2(3H)-one,
3-(3-chloro-2-fluoro-4-trifluoromethoxy-phenyl)-5-(2,6-difluorophenyl)-1,3,4-oxadiazol-2(3H)-one,
3-(2,3-dichloro-5-trifluoromethyl-phenyl)-5-(2,6-difluorophenyl)-1,3,4-oxadiazol-2(3H)-one,
3-(3-chloro-2-fluoro-5-trifluoromethyl-phenyl)-5-(2,6-difluorophenyl)-1,3,4-oxadiazol-2(3H)-one, 3-(2-chloro-3-trifluoromethyl-phenyl)-5-(2,6-difluorophenyl)-1,3,4-oxadiazol-2(3H)-one,
5-(2-chloro-6-fluorophenyl)-3-(3-fluoro-o-tolyl)-1,3,4-oxadiazol-2(3H)-one,
3-(3-chloro-2,5-dimethylphenyl)-5-(2-chloro-6-fluorophenyl)-1,3,4-oxadiazol-2(3H)-one,
5-(2-chloro-6-fluorophenyl)-3-(2,3,5-trifluorophenyl)-1,3,4-oxadiazol-2(3H)-one,
5-(2,6-difluorophenyl)-3-[2-(1,1,2,2-tetrafluoroethoxy)-phenyl]-1,3,4-oxadiazol-2(3H)-one,
3-(4-chloro-3-chlorodifluoromethoxy-phenyl)-5-(2,6-difluorophenyl)-1,3,4-oxadiazol-2(3H)-one,
3-(2-chlorophenyl)-5-(2-fluoro-6-methoxyphenyl)-1,3,4-oxadiazol-2(3H)-one,
3-(2-chlorophenyl)-5-(2-trifluoromethoxy-phenyl)-1,3,4-oxadiazol-2(3H)-one,
5-(2-chloro-6-fluorophenyl)-3-[2-(2-chloroethoxy)-phenyl]-1,3,4-oxadiazol-2(3H)-one,
3-(3-chloro-2-fluorophenyl)-5-(2-chloro-6-fluorophenyl)-1,3,4-oxadiazol-2(3H)-one,
3-(3-chloro-2-fluorophenyl)-5-(2-chloro-6-fluorophenyl)-1,3,4-oxadiazole-2(3H)-thione,
5-(2-chloro-6-fluorophenyl)-3-(2,3-dichlorophenyl)-1,3,4-oxadiazol-2(3H)-one,
5-(2-chlorophenyl)-3-(3-chloro-o-tolyl)-1,3,4-oxadiazol-2(3H)-one,
3-(3-chloro-2-fluorophenyl)-5-(2,6-difluorophenyl)-1,3,4-oxadiazol-2(3H)-one,
3-(2-chloro-6-fluoro-4-trifluoromethyl-phenyl)-5-(2,6-difluorophenyl)-1,3,4-oxadiazol-2(3H)-one,
3-(2-chloro-4-trifluoromethoxy-phenyl)-5-(2,6-difluorophenyl)-1,3,4-oxadiazol-2(3H)-one,
5-(2-chloro-6-fluorophenyl)-3-(2-fluoro-4-trifluoromethylthio-phenyl)-1,3,4-oxadiazol-2(3H)-one,
3-[4-(2-chloro-1,1,2-trifluoroethylthio)-2-fluorophenyl]-5-(2,6-difluorophenyl)-1,3,4-oxadiazol-2(3H)-one,
5-(2,6-difluorophenyl)-3-(4-fluoro-2-trifluoromethoxyphenyl)-1,3,4-oxadiazol-2(3H)-one,
5-(2-chlorophenyl)-3-[4-(2,2-dichloro-1,1-difluoroethoxy)-phenyl]-1,3,4-oxadiazol-2(3H)-one,
5-(2,6-difluorophenyl)-3-(4-trifluoromethoxy-3-trifluoromethyl-phenyl)-1,3,4-oxadiazol-2(3H)-one,
3-(2-chloro-m-tolyl)-5-(2,6-difluorophenyl)-1,3,4-oxadiazole-2(3H)-thione,
5-(2-chloro-6-fluorophenyl)-3-(2,3-dichlorophenyl)-1,3,4-oxadiazole-2(3H)-thione,
3-(2-chlorophenyl)-5(2-chloro-4-fluorophenyl)-1,3,4-oxadiazole-2(3H)-thione,
3-(2-bromophenyl)-5-(2,6-difluorophenyl)-1,3,4-oxadiazole-2(3H)-thione,
3-(2-chlorophenyl)-5-(2,6-difluorophenyl)-1,3,4-oxadiazole-2(3H)-thione,
5-(2-chloro-6-fluorophenyl)-3-(2-fluorophenyl)-1,3,4-oxadiazole-2(3H)-thione,
5-(2-chlorophenyl)-3-(α,α,α-trifluoro-o-tolyl)-1,3,4-oxadiazole-2(3H)-thione,
5-(2-chlorophenyl)-3-(3-chloro-o-tolyl)-1,3,4-oxadiazole-2(3H)-thione,
3-(3-chloro-2-fluorophenyl)-5-(2,6-difluorophenyl)-1,3,4-oxadiazole-2(3H)-thione,
3-(2,3,4,5-tetrafluorophenyl)-5-(2,4,6-trifluorophenyl)-1,3,4-oxadiazole-2(3H)-thione,
5-(2,6-difluorophenyl)-3-(2-fluorophenyl)-1,3,4-oxadiazol-2(3H)-one,
5-(2-chloro-6-fluorophenyl)-3-(2-chloro-3-pyridyl)-1,3,4-oxadiazol-2(3H)-one,
3-(2-chloro-5-methoxy-phenyl)-5-(α,α,α-trifluoro-o-tolyl)-1,3,4-oxadiazol-2(3H)-one,
3-(3,4-dichlorophenyl)-5-(α,α,α-trifluoro-o-tolyl)-1,3,4-oxadiazol-2(3H)-one,
5-(2,6-difluorophenyl)-3-(α,α,α-trifluoro-o-tolyl)-1,3,4-thiadiazole-2(3H)-thione,
3-(2,6-dichloro-4-trifluoromethoxy-phenyl)-5-(2,6-difluorophenyl)-1,3,4-oxadiazol-2(3H)-one,
3-[2-chloro-4-(1,1,2,3,3,3-hexafluoropropoxy)-3-trifluoromethyl-phenyl]-5-(2,6-difluorophenyl)-1,3,4-oxadiazol-2(3H)-one,
5-(2-chloro-6-fluorophenyl)-3-(2,4-dimethylphenyl)-1,3,4-oxadiazole-2(3H)-thione,
3-(3-chloro-o-tolyl)-5-(2,6-difluorophenyl)-1,3,4-oxadiazole-2(3H)-thione,
3-(2,6-dichloro-4-trifluoromethyl-phenyl)-5-(2,6-difluorophenyl)-1,3,4-oxadiazole-2(3H)-thione,
3-(2,6-dichloro-4-trifluoromethoxy-phenyl)-5-(2,6-difluorophenyl)-1,3,4-oxadiazole-2(3H)-thione and
3-[2-chloro-4-(2-chloro-1,1,2-trifluoroethoxy)-5-trifluoromethyl-phenyl]-5-(2,6-difluorophenyl)-1,3,4-oxadiazole-2(3H)-thione.

The process in accordance with the invention for the manufacture of the compounds of formula I comprises (a) for the manufacture of those compounds of formula I in which X signifies oxygen or sulfur, reacting a hydrazide of the general formula

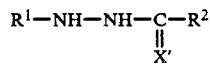

wherein $R^1$ and $R^2$ have the significances given above and X' signifies oxygen or sulfur, with phosgene, trichloromethyl chloroformate or a lower alkyl chloroformate (Y=oxygen) or with thiophosgene or carbon disulfide (Y=sulfur), (b) for the manufacture of those compounds of formula I in which X signifies $NR^3$ and Y signifies oxygen, subjecting a 2,4-dihydro-3H-1,2,4-triazol-3-one of the general formula

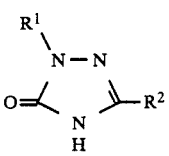

wherein $R^1$ and $R^2$ have the significances given above,
to an alkylation, or (c) for the manufacture of those compounds of formula I in which Y signifies sulfur, treating a compound of the general formula

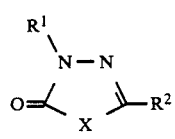

wherein $R^1$, $R^2$ and X have the significances given above,
with a sulfurizing agent.

When phosgene, trichloromethyl chloroformate or thiophosgene is used, the reaction according to process variant (a) is conveniently carried out by treating a solution or suspension of the hydrazide of formula II in an inert solvent or diluent such a chlorinated aliphatic hydrocarbon, e.g. methylene chloride or chloroform; an aromatic hydrocarbon, e.g. toluene; a lower alkyl acetate, e.g. ethyl acetate; or an aliphatic or cyclic ether, e.g. dioxan, with a solution of phosgene or thiophosgene in the same solvent or diluent, especially in toluene; or with liquid trichloromethyl chlorofomate ("diphosgene"), preferably at temperatures between room temperature and the reflux temperature of the reaction mixture, particularly in the temperature range of 55° C. to 110° C. The reaction is preferably carried out with a slight excess of phosgene, diphosgene or thiophosgene, in which case the molar ratio hydrazide II: phosgene or thiophosgene amounts to about 1:1.05–5 and the molar ratio hydrazide II: diphosgene amounts to about 1:0.55–2.5.

In the reaction there can initially take place at least to some extent an addition reaction, with an intermediate of general formula IV

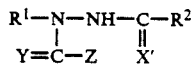     IV wherein $R^1$, $R^2$, $X'$ and Y have the significances given above and Z signifies chlorine or trichloromethoxy, being formed. The cyclization of IV can be effected by evaporating off the excess phosgene or thiophosgene, again taking up the residual crude mixture in an inert solvent such as a chlorinated aliphatic hydrocarbon, e.g. methylene chloride; an aromatic hydrocarbon, e.g. toluene; a lower alkanol, e.g. methanol; or an aliphatic or cyclic ether, e.g. tetrahydrofuran, and heating the solution at reflux temperature for a short time in the presence of an auxiliary base, e.g. triethylamine, an optionally alkyl-substituted pyridine, 4-dimethylaminopyridine or N,N-dimethylaniline. The molar ratio of base: hydrazide II used conveniently amounts to about 1.0 to 2.0:1.

When a lower alkyl chloroformate, especially ethyl chloroformate, is used as the second reactant, the reaction is conveniently effected in the presence of a diluent such as a chlorinated aliphatic hydrocarbon, e.g. chloroform; an aromatic hydrocarbon, e.g. toluene; an aliphatic or cyclic ether, e.g. tetrahydrofuran; or acetonitrile, and using an auxiliary base, e.g. triethylamine, at temperatures of 0° C. to the reflux temperature of the reaction mixture. Stoichiometric amounts of hydrazide and ester are conveniently used or the reaction is carried out with a slight excess, i.e. up to a 40% excess, of ester. The auxiliary base is also used in stoichiometric amount or in a slight excess, i.e. up to about 40% excess. In this reaction there initially takes place an addition reaction, with an intermediate of general formula IV given above in which $R^1$, $R^2$, $X'$ and Y have the significances given above and Z signifies lower alkoxy, especially ethoxy, being formed. This intermediate is then cyclized by heating, optionally in the presence of a diluent such as an optionally chlorinated aromatic hydrocarbon, e.g. xylene or o-dichlorobenzene, and conveniently using a catalytic amount of a base, e.g. dimethylaminopyridine. However, the cyclization is preferably carried out in the melt, i.e. in the temperature range of 120° C. to 200° C. For further details concerning the reaction of a hydrazide with a lower alkyl chloroformate reference is made to J. Het. Chem., 23, 417 (1986).

When carbon disulfide is used as the second reactant in process variant (a), the reaction is also conveniently effected in the presence of a diluent such as, for example, ethanol, 2-methoxyethanol or water, and using a base, e.g. potassium hydroxide, sodium methylate or dimethylamine, at temperatures of 0° C. to the reflux temperature of the reaction mixture. The carbon disulfide and the base are each used in stoichiometric amounts or in a slight excess of up to about 40%. In this reaction too there initially takes place an addition reaction, with in this case an intermediate of general formula IV given above in which $R^1$, $R^2$ and $X'$ have the significances given above and Y and Z signify sulfur being obtained as a salt. This salt is then cyclized by treatment with a mineral acid, e.g. hydrochloric acid, conveniently in the same diluent and/or water.

In process variant (b) the term "alkylating" stands for the introduction of a methyl, halomethyl or 2-propynyl group ($R^3$) on the unsubstituted nitrogen atom (-NH-) of the triazole nucleus. A methyl, halomethyl or 2-propynyl halide, e.g. methyl iodide, difluorochloromethane or pro-pargyl bromide, or dimethyl sulfate is conveniently used as the alkylating agent. The alkylation is conveniently effected in an inert diluent in which the starting material III is either dissolved or suspended and, more- over, preferably in the presence of an acid-binding agent. Suitable diluents are especially aliphatic ketones, e.g. acetone and methyl ethyl ketone; aliphatic and cyclic ethers, e.g. dimethoxyethane and tetrahydrofuran, aromatic hydrocarbons, e.g. toluene; acetonitrile; dimethylform- amide; dimethylpropyleneurea; dimethyl sulfoxide; alcohols, e.g. ethanol and 2-methoxyethanol; and water. Examples of suitable acid-binding agents are sodium hydride; alkali metal carbonates, e.g. sodium carbonate and potassium carbonate; alkali metal bicarbonates, e.g. sodium bicarbonate; and trialkylamines, e.g. triethyl- amine. These agents are preferably used in stoichiometric amount or even in excess, i.e. in the molar equivalent range of 1.0 to about 5.0. Moreover, catalytic amounts (about 1 to 10 weight percent) of dimethylaminopyridine are preferably present. The reaction temperatures can be varied in a wide range in carrying out this process variant, whereby in general it is carried out at temperatures between −20° C. and 160° C., preferably between 20° C. and 80° C.

A byproduct of the general formula

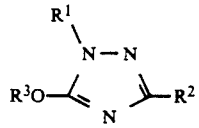

wherein $R^1$, $R^2$ and $R^3$ have the significances given above, can form in the alkylation. This byproduct is normally present in a relatively small amount, i.e. up to about 5 weight percent, and itself has pesticidal properties, although in general less pronounced than in the case of the compounds I in accordance with the invention. The byproduct can be separated from the main product of formula I according to usual methods, e.g. chromatography or fractional crystallization.

For the sulfurization according to process variant (c) there is conveniently used phosphorus pentasulfide, optionally in the presence of pyridine, e.g. as the phosphorus pentasulfide-pyridine (1:2) complex, the Lawesson reagent 2,4-bis-(4-methoxyphenyl)-1,2-dithioxo- 1,3,2,4-dithiaphosphetane [see e.g. S. -O. Lawesson et al., Bull. Soc. Chim. Belg. 87, 229-238 (1978)] or the Davy reagent 2,4-bis-(methylthio)-1,3,2,4-dithiadiphosphetane (see e.g. Sulfur Lett. 1983, 1, 167), with this being preferably used in stoichiometric amount or in a slight excess (e.g. up to 20%). The reaction is conveniently carried out in an inert organic diluent such as an optionally halogenated aromatic, e.g. toluene or dichlorobenzene, or an aliphatic or cyclic ether, e.g. dimethoxyethane, and at elevated temperature, especially at temperatures between 80° C. and the reflux temperature of the reaction mixture. Moreover, a catalytic amount, i.e. about 0.1 to 10 weight percent, based on the amount of the compound I', of hexamethylphosphortriamide is advantageously added.

The isolation and the purification of the thus-manufactured compounds of formula I can be effected according to methods known per se, e.g. recrystallization, distillation or column chromatography.

The hydrazides of formula II in which X' signifies oxygen, which are used as starting materials in process variant (a), are either known or can be produced in a manner known per se, for example by reacting corresponding hydrazines of the general formula $$R^1-NH-NH_2 \quad\quad V$$

wherein $R^1$ has the significance given above,
or their acid addition salts, e.g. hydrochlorides, with substituted benzoyl halides or lower alkyl benzoates of the general formula $$R^2-COR^4 \quad\quad VI$$

wherein $R^2$ has the significance given above and $R^4$ signifies fluorine, chlorine or bromine, or lower alkoxy, especially $C_{1-3}$-alkoxy, in the presence of a base such as, for example, pyridine, triethylamine, sodium hydroxide, calcium hydroxide, potassium carbonate or calcium oxide under the reaction conditions which are familiar to the person skilled in the art. Thus, for example, the hydrazine V or an acid addition salt thereof in an inert diluent, such as an aliphatic or aromatic hydrocarbon, e.g. toluene, an aliphatic or cyclic ether, e.g. tert.butyl methyl ether or tetrahydrofuran, an aliphatic ester, e.g. ethyl acetate, an alcohol, e.g. ethanol; water; or a mixture of two or more of these diluents is treated with the benzoic acid derivative VI. In a preferred embodiment, an acid addition salt, e.g. the hydrochloride, of the hydrazine V is placed in water and the aqueous medium is covered with a water-immiscible organic solvent, e.g. toluene, tert.butyl methyl ether or, preferably, ethyl acetate. By adding an inorganic base as the acid-binding agent, e.g. sodium hydroxide, sodium carbonate, potassium carbonate or calcium oxide, there is firstly liberated the hydrazine V and this is taken up in the organic phase. This base is conveniently used in stoichiometric amount or in an excess of up to a 4:1 molar ratio based on the amount of hydrazine salt. Subsequently, the benzoyl fluoride or benzoyl chloride VI ($R^4$=fluorine or chlorine), optionally dissolved in the solvent used, is added dropwise to the organic phase in which the reaction then takes place. The liberated acid is thereby taken up in the aqueous phase. The isolation of the hydrazine II is conveniently effected by separating the organic phase, followed by removal of the organic solvent, e.g. by distillation.

In general, the reaction temperatures lie between $-20°$ C. and the boiling point of the diluent which is used, preferably between 0° C. and 80° C., or between 5° C. and about 30° C. when a two-phase system is used. In the latter case, the reaction is preferably carried out at room temperature.

The hydrazides of formula II in which X' signifies sulfur, which are used as starting materials in process variant (a), can be produced by treating a hydrazide of formula II in which X' signifies oxygen with a sulfurizing agent such as the above-mentioned Lawesson reagent in toluene, conveniently under the reaction conditions mentioned above in connection with process variant (c).

A further method for the production of these hydrazides comprises treating a benzhydrazinoyl chloride of the general formula

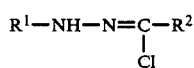

$$R^1-NH-N=C-R^2 \quad\quad VII$$
$$\underset{Cl}{|}$$

wherein $R^1$ and $R^2$ have the significances given above,
with hydrogen sulfide in the present of a base, e.g. triethylamine. This process is described in more detail inter alia in Can. J. Chem., 52, 879 (1974).

The 2,4-dihydro-3H-1,2,4-triazol-3-ones of formula III, which are used as starting materials of process variant (b), are in part known from European Patent Publication No. 208 321 and can be produced e.g. in accordance with the following Reaction Schemes 1 and 2:

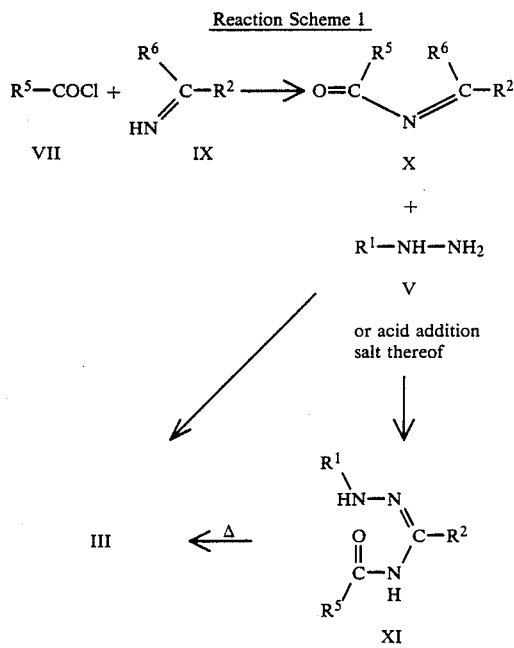

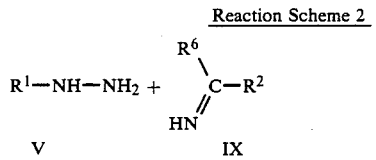

-continued
Reaction Scheme 2

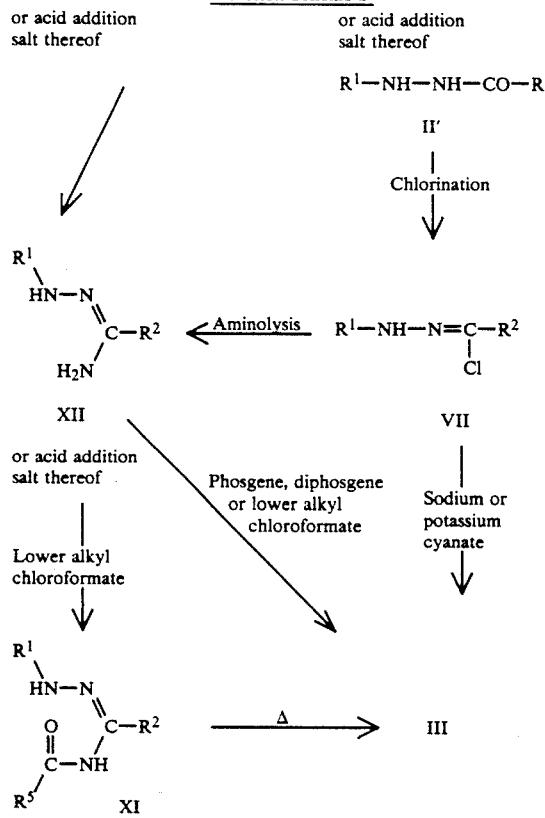

In the Reaction Schemes $R^1$ and $R^2$ have the significances given above; $R^5$ and $R^6$ signify lower alkoxy, especially $C_{1-3}$-alkoxy such as methoxy or ethoxy.

The first method for the production of the starting materials III (Reaction Scheme 1) comprises reacting a lower alkyl chloroformate of formula VIII with an alkyl benzimidate of formula IX and reacting the thus-produced N-alkoxycarbonyl-benzimidate of formula X with a hydrazine of formula V or with an acid addition salt thereof. The first step is conveniently effected in the presence of a base, especially a sterically hindered base such as 2,6-lutidine or sym-collidine, and in the presence of an inert diluent such as a hydrocarbon, e.g. n-heptane or petrol, at an elevated temperature, e.g. at the reflux temperature of the reaction mixture. This process is exemplified, for example, in Synthesis 1983, 483–6. The reaction of the compound of formula X with the hydrazine of formula V or with an acid addition salt thereof, e.g. a salt with a mineral acid such as hydrochloric acid or sulfuric acid or with an organic acid such as oxalic acid, is conveniently effected in an inert diluent such as a chlorinated aliphatic or aromatic hydrocarbon, e.g. carbon tetrachloride, 1,1,2-trichloroethane or 1,2-dichlorobenzene; an alcohol, e.g. ethanol or 2-methoxyethanol; an aliphatic or cyclic ether, e.g. diethylene glycol diethyl ether, tetrahydrofuran or dioxan; an aliphatic nitrile, e.g. acetonitrile; an aliphatic or aromatic hydrocarbon, e.g. n-heptane, toluene or o- or p-xylene; or dimethylformamide. When a mineral salt or an organic salt of the hydrazine of formula V is used, the reaction is also preferably carried out in the presence of an acid-binding agent, e.g. triethylamine, 6-ethyl-2-methylpyridine, 2,6-lutidine or sodium acetate. The reaction temperatures can be varied in a wide range, whereby in general the reaction is carried out at temperatures between 20° C. and the reflux temperature of the reaction mixture, preferably between 80° C. and 120° C.

In accordance with Scheme 1 there can, however, take place initially only a hydrazine addition with the formation of a compound of formula XI. After isolation the compound can be converted by heating to about 140°-220° C. (in the melt) with cleavage of the lower alkanol $R^5H$ into the corresponding 2,4- or 1,2-dihydro-3H-1,2,4-triazol-3-one of formula III or III', respectively

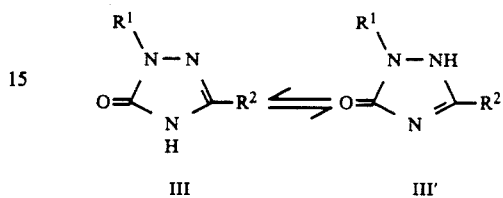

The isolation of the compound XI is, however, not necessary: where the N-alkoxycarbonyl-benzimidate X is reacted with the hydrazine V in an optionally chlorinated aromatic hydrocarbon such as toluene or 1,2-dichlorobenzene at temperatures between 0° C. and 80° C. and the mixture is subsequently heated to about 110°-160° C., the compound XI forms. The alkanol $R^5H$ which is formed is conveniently distilled off azeotropically from the reaction mixture.

In the second method for the production of the starting materials III (Reaction Scheme 2) the essential process step is the cyclization of the amidrazone of formula XII or an acid addition salt thereof, e.g. the hydrochloride, with phosgene, diphosgene or a lower alkyl (preferably $C_{1-3}$-alkyl) chloroformate, conveniently in the presence of an inert diluent and using an acid-binding agent. Especially suitable diluents are chlorinated aliphatic or aromatic hydrocarbons, e.g. 1,1,2-trichloroethane and 1,2-dichlorobenzene; aliphatic or cyclic ethers, e.g. diethylene glycol diethyl ether, tetrahydrofuran and dioxan; aliphatic nitriles, e.g. acetonitrile; aliphatic or aromatic hydrocarbons, e.g. toluene and o- and/or p-xylene; and pyridine. A tertiary amine such as triethylamine or pyridine is preferably used as the acid-binding agent. The reaction temperatures can be varied in a wide range, with the reaction being conveniently carried out at temperatures between 0° C. and the reflux temperature of the reaction mixture.

Occasionally in this method, especially when a lower alkyl chloroformate is used, there initially takes place only a carbamoylation, with a compound of formula XI in which $R^5$ signifies lower alkoxy being formed initially. This compound can, optionally after isolation, be converted into the corresponding 2,4-dihydro-3H-1,2,4-triazol-3-one of formula III under the reaction conditions of Scheme 1.

A further method for the production of the starting materials III comprises reacting a benhydrazinoyl chloride of formula VII with sodium cyanate or potassium cyanate [see Reaction Scheme 2 as well as Gazz. Chim. Ital. 68, 147 (1968)]. The reaction is conveniently effected in an inert diluent such as ethanol, acetone, acetonitrile, acetic acid, tetrahydrofuran, dimethylformamide, water or a mixture of two or more of these diluents, e.g. an ethanol/water or acetone/water mixture. About 5 to 25 percent by volume of water is preferably present in such mixtures. The reaction temperatures can be varied in a wide range, i.e. from about −10° C. to the reflux temperature of the reaction mixture. The sodium cyanate or potassium cyanate is used in stoichiometric amount or in a slight excess, i.e. in up to a 3:1 molar ratio based on the amount of benzhydrazinoyl chloride VII.

The amidrazones XII themselves and their acid addition salts are either known or can be produced in a manner known per se, for example by reacting a hydazine of formula V or an acid addition salt thereof, e.g. the hydrochloride, with an alkyl benzimidate of formula IX or with an acid addition salt thereof, e.g. the hydrochloride or tetrafluoroborate salt. If desired, the reaction is effected in an inert diluent, such as a chlorinated aliphatic hydrocarbon, e.g. methylene chloride; an aromatic, e.g. toluene; an aliphatic or cyclic ether, e.g. tetrahydrofuran or dioxan; a lower alkanol, e.g. ethanol; or pyridine, at relatively low temperatures, e.g. between 0° C. and about 60° C. The starting materials of formulae V and IX are advantageously used in stoichiometric amount.

A further method for the production of these amidrazones comprises treating a hydrazide of formula II' with phosphorus oxychloride optionally in a slight excess, i.e. with about 1.005 to 4, particularly with about 1.02 to 1.15, equivalents of phosphorus oxychloride per equivalent of hydrazide, at temperatures between 85° C. and 110° C. and optionally in the presence of a diluent such as, for example, toluene, dioxan or 1,2-dichloroethane, particularly at 100° C. in the presence of toluene, in order to produce the corresponding benzhydrazinoyl chloride of formula VII and then subjecting this to an aminolysis. For this purpose, for example, a solution of the benzhydrazinoyl chloride in an inert solvent such as an aromatic, e.g. toluene, or an aliphatic or cyclic ether, e.g. diethyl ether or dioxan, is treated at about −40° C. to 20° C. with a solution of ammonia in ethanol or water or with gaseous ammonia. Especially preferably, the reaction mixture of the chlorination is introduced directly into a well-cooled mixture of aqueous ammonia in dioxan or ethanol or of dry ammonia in diethyl ether or ethanol and the product of formula XII is then separated by extraction with a suitable acid, e.g. hydrochloric acid, as the corresponding salt in aqueous solution. The amidrazone XII can be isolated in pure form by the addition of a base, e.g. sodium hydroxide solution. In this procedure it is advantageous to carry out the amino-lysis at low temperatures, e.g. between −50° C. and 10° C., preferably between −20° C. and 5° C., especially because the benzylhydrazinoyl chloride VII is usually inclined to dimerize.

As an alternative to the direct treatment of the reaction mixture of the chlorination with ammonia, this reaction mixture can be taken up in water and the benzhydrazinoyl chloride VII can be extracted from the aqueous phase with a suitable organic solvent while stirring well. The excess chlorinating agent is thereby removed. Suitable organic solvents for this purpose are aliphatic ethers, e.g. diethyl ether and tert.butyl methyl ether, chlorinated aliphatic hydrocarbons, e.g. methylene chloride, and aliphatic or aromatic hydrocarbons, e.g. n-hexane and toluene. However, aqueous-organic mixtures, e.g. toluene/water mixtures, are preferably used. If desired, prior to the extraction the aqueous phase can be adjusted to a pH value in the range of 2 to 7 by adding a base. After carrying out the extraction the benzhydrazinoyl chloride can be isolated from its solution in the organic solvent and subjected to the subsequent aminolysis, to give the amidrazone XII, or to the direct reaction with sodium cyanate or potassium cyanate, to give the 2,4-dihydro-3H-1,2,4-triazol-3-one III.

The compounds of formula I', which are used as starting materials of process variant (c), are obtainable, in view of their being a sub-group of the compounds of formula I, in accordance with process variant (a) (X=oxygen or sulfur) or (b) (X=NR$^3$).

The remaining starting materials or reagents, i.e. inter alia the compounds of formulae V (and their acid addition salts), VI, VIII and XII, are either known or can be produced according to methods known per se. The isolation and the purification of the thus-produced starting materials can also be effected in a manner known per se.

The compounds in accordance with the invention, i.e. the compounds of formula I, are quite generally of value as pesticides. They have been found to be particularly valuable for the control of insects and mites, especially of Homoptera (especially aphids) such as e.g.
*Aphis fabae, Aphis gossypii, Aphis pomi;*
*Acyrthosiphon pisum, Acyrthosiphon dirhodum;*
*Brevicoryne brassicae;*
*Dysaphis devecta, Dysaphis pyri, Dysaphis plantaginea;*
*Macrosiphum rosae; Macrosiphum avenae;*
*Myzus persicae, Myzus cerasi;*
*Phorodon humuli;*
*Rhopalosiphum insertum, Rhopalosiphum padi;*
*Toxoptera aurantii;*
*Nasonovia ribisnigri;*
*Hyalopterus pruni;*
Leaf lice (Psyllina) such as e.g. *Psylla piri, Psylla pirisuga, Psylla piricola, Psylla mali; Trioza apicalis;*
white flies such as e.g. *Trialeurodes vaporariorum; Aleurothrixus floccosus; Bemisia tabaci; Aleurodes proletella; Aleurocanthus woglumi; Dialeurodes citri;*
mites which are of importance in plant protection, such as e.g.
Tetranychidae (spider mites), especially *Tetranychus urticae, Tetranychus cinnabarinus, Tetranychus turkestani, Tetranychus McDanieli, Tetranychus kanzawai; Panonychus ulmi, Panonychus citri;*
*Phyllocoptruta oleivora;*
*Aculus schlechtendali;*
*Phyllocoptes vitis;*
*Aceria essigi, Aceria gracilis; Cecidophyopsis ribis;*
*Eriophyes vitis;*
*Eotetranychus sexmaculatus, Eotetranychus carpini;*
*Hemitarsonemus latus;*
mites which are of importance in veterinary medicine such as e.g.
*Macronyssus bursa, Macronyssus sylviarum, Macronyssus lacoti;*
*Dermanyssus gallinae;*
ticks, especially of the families Ixodidae and Argasidae and of the orders Boophilus, Amblyomma, Hyalomma, Rhipicephalus, Ixodes, Argas and Ornithodorus.

The compounds in accordance with the invention act as contact and feed poisons. Moreover, some of the compounds are taken up by various plants, so that the pests to be controlled are killed when they eat the plants. These compounds thus exhibit systemic activity.

The pest control composition in accordance with the invention contains an effective amount of at least one compound of general formula I, as defined above, as well as formulation adjuvants. The composition conveniently contains at least one of the following formulation adjuvants:

Solid carrier substances; solvents or dispersion media; tensides (wetting and emulsifying agents); dispersing agents (without tenside action); and stabilizers.

With the use of these and, if desired, additional adjuvants the compounds of formula I can be converted into the usual formulations such as solutions, suspensions, emulsions, emulsifiable concentrates, pastes, foams, dusts, powders and granulates.

As solid carrier substances there essentially come into consideration: natural mineral substances such as kaolin, aluminas, siliceous earth, talc, bentonite, chalk, limestone, quartz, dolomite, attapulgite, montmorillonite and diatomaceous earth; synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as dusts, powders or granulates.

As solvents or dispersion media there essentially come into consideration: aromatics such as toluene, xylenes, benzene and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol as well as their ethers and esters; ketones such as acetone, methyl isobutyl ketone and cyclohexanone; and strongly polar solvents such as dimethylformamide, N-methylpyrrolidone and dimethyl sulfoxide, such solvents or dispersion media preferably having flash points of at least 30° C. and boiling points of at least 50° C., and water. Among the solvents or dispersion media there also come into consideration so-called liquified gaseous extenders or carrier substances, these being products which are gaseous at room temperature and under normal pressure. Examples of such products are especially aerosol propellants such as halogenated hydrocarbons, e.g. dichlorodifluoromethane. When water is used as the solvent, organic solvents can e.g. also be used as auxiliary solvents.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulfate esters, e.g. dodecyl sodium sulfate, octadecyl sodium sulfate and cetyl sodium sulfate; alkyl sulfonates, aryl sulfonates and fatty-aromatic sulfonates such as alkylbenzenesulfonates, e.g. calcium dodecylbenzenesulfonate, and butylnaphthalenesulfonates; and more complex fatty sulfonates, e.g. the amide condensation products of oleic acid and N-methyltaurine and the sodium sulfonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration: lignin, sodium and ammonium salts of lignin sulfonic acids, sodium salts of maleic anhydride-diisobutylene copolymers, sodium and ammonium salts of sulfonated polycondensation products from naphthalene and formaldehyde, and sulfite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents e.g. epichlorohydrin, phenyl glycidyl ether and soya epoxides; antioxidants e.g. gallic acid esters and butylhydroxytoluene; UV-absorbers e.g. substituted benzophenones, diphenylacrylonitrile acid esters and cinnamic acid esters; and deactivators e.g. salts of ethylenediaminotetraacetic acid and polyglycols.

The pest control compositions in accordance with the invention can contain, in addition to the active substances of formula I, other active substances, e.g. other pest control agents, pest baits, fungicides, bactericides, herbicides, plant growth regulators and fertilizers. Such combination compositions are suitable for intensifying the activity or for broadening the spectrum of activity. If desired, insufficiencies of hitherto known added agents can thereby also be compensated for.

It has been found that the compounds in accordance with the invention, especially the particularly preferred compounds, are advantageously used in combination with other acaricides, primarily with acaricides which are suitable for the control of mobile states of mites. Examples of such acaricides are amitraz, avermectin, benzoxinate, bromopropylate, chlorobenzilate, cyhexatin, dicofol, fenbutatin oxide, methidathion, propargite and ethyl 5,7-dihydro-6H-dibenz[c,e]azepine-6-carboximidate as well as pyrethroids having acaricidal activity such as, for example, fluvalinate, biphenthrin and cyano-3-phenoxybenzyl-3-(2-chloro-2,3,3-trifluoroprop-1-enyl)-2,2-dimethyl-cyclopropanecarboxylate. The use can be effected as a mixture or separately. Thereby, the active substances in accordance with the invention can compensate for the disadvantage of the known acaricides having a main focus of activity against adult pests, in that the eggs and larvae which survive after the use of the known acaricides and which can develop rapidly to a new adult population are also killed.

The pest control compositions in accordance with the invention generally contain between 0.005 and 95 weight percent of the compound(s) of formula I in accordance with the invention as the active substance(s). They can be present in a form which is suitable for storage and transport. In such forms, e.g. emulsifiable concentrates, the active substance concentration is normally in the higher region of the above concentration range. These forms can be diluted with the same or different formulation adjuvants to give active substance concentrations which are suitable for practical use and such concentrations normally lie in the lower region of the above concentration range. Emulsifiable concentrates generally contain 5 to 95 weight percent, preferably 10 to 80 weight percent, of the compound(s) in accordance with the invention. As application forms there come into consideration, inter alia, ready-for-use solutions, emulsions, suspensions, foams, powders, pastes, dusting compositions and granulates. The active substance concentrations in such ready-for-use compositions can be varied in wide limits. In spray liquors there can be present e.g. concentrations between 0.005 and 0.5 weight percent. In the Ultra-Low-Volume process there can be formulated spray liquors in which the active substance concentration is preferably from 10 to 20 weight percent, while the spray liquors formulated in the Low-Volume process and in the High-Volume process preferably have an active substance concentration of 0.01 to 0.5 and 0.005 to 0.1 weight percent, respectively. Granulates preferably contain from 5 to 50 weight percent of the compound (s) in accordance with the invention as the active substance.

The pest control compositions in accordance with the invention can be manufactured by mixing at least one compound of general formula I with formulation adjuvants.

The manufacture of the compositions can be carried out in a known manner, e.g. by mixing the active substance with solid carrier substances, by dissolution or suspension in suitable solvents or dispersion media, if necessary using tensides as wetting or emulsifing agents, or dispersing agents, by diluting pre-prepared emulsifiable concentrates with solvents or dispersion media, etc.

In the case of pulverous compositions the active substance can be mixed with a solid carrier substance, e.g. by grinding together; or the solid carrier substance can be impregnated with a solution or suspension of the active substance and then the solvent or suspension medium can be removed by evaporation, by heating or by sucking-off under reduced pressure. By adding tensides or dispersing agents such pulverous compositions can be made readily wettable with water, so that they can be converted into aqueous suspensions which are suitable e.g. as spray compositions.

The compounds of formula I can also be mixed with a tenside and a solid carrier substance to form a wettable powder which is dispersible in water or they can be mixed with a solid pre-granulated carrier substance to form a product in the form of a granulate.

If desired, the compound of formula I can be dissolved in a water-immiscible solvent such as, for example, an alicyclic ketone, which conveniently contains a dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The method in accordance with the invention for the control of pests comprises by treating the locus to be protected or the pests themselves with an effective amount of a compound in accordance with the invention or of a pest control composition in accordance with the invention. This method of use can be carried out by application to the soil or leaves or by application to the animals, supplies or materials to be protected, depending on the kind of pests to be controlled. The control is achieved, for example, by contact or by intake with the feed.

The use can be carried out in a conventional manner, e.g. by sprinkling, spraying, atomizing, dusting, scattering, drilling-in, smoking, watering, steeping or coating. Pulverous preperations can be applied to the pests or to the locus to be protected, e.g. plants or animals, as e.g. dusting agents with the aid of the usual dusting appliances. Aqueous suspensions can be used e.g. as spray compositions.

When used in plant protection there is usually sufficient a dosage of about 50–500 g of active substance [compound(s) of formula I]/ha, e.g. as is the case in the application of 2000 l of a spray liquor which contains 0.0025–0.025 weight percent of active substance to 1 ha of cultivated land.

The following Examples serve to illustrate the invention in more detail.

I. Manufacture of the active substances of formula I:

EXAMPLE 1

2.5 g (7.5 mmol) of 2-chloro-6-fluoro-N'-($\alpha,\alpha,\alpha$-trifluoro-o-tolyl)-benzhydrazide are heated to reflux temperature (internal temperature 80° C.) for 16 hours in 35 ml of a 20% solution of phosgene (67 mmol) in toluene. Excess phosgene and toluene are then distilled off, and the residue is dissolved in 30 ml of methylene chloride and heated to reflux temperature for 30 minutes with the addition of 6.7 ml (48 mmol) of triethylamine. The mixture is subsequently washed with water, dried over anhydrous sodium sulfate and evaporated under reduced pressure. After chromatographic purification of the crude product with toluene/n-hexane (1:1) as the eluent and recrystallization from methylene chloride/n-hexane there is obtained pure 5-(2-chloro-6-fluorophenyl)-3-($\alpha,\alpha,\alpha$-trifluoro-o-tolyl)-1,3,4-oxadiazol-2(3H)-one, m.p. 109°–109.5° C.; IR spectrum: 1792 cm$^{-1}$; mass spectrum: 358(14), 314(23), 159(100).

EXAMPLE 2

39 g (0.13 mol) of 2-chloro-6-fluoro-N'-(o-chlorophenyl)-benzhydrazide are treated with a solution of 40 g (0.40 mol) of phosgene in 275 ml of toluene and the mixture is heated to reflux temperature (internal temperature 59° C.) for 2.5 hours. A further 13 g (0.13 mol) of phosgene in 70 ml of toluene are added thereto and the reaction mixture is heated to reflux temperature for a further 2.5 hours. The excess phosgene and toluene are distilled off, and the residue is taken up in 500 ml of diethyl ether and the solution is washed with semisaturated sodium chloride solution, dried over anhydrous magnesium sulfate and evaporated under reduced pressure. After recrystallization of the crude product from a mixture of diethyl ether and n-hexane there is obtained pure 5-(2-chloro-6-fluorophenyl)-3-(2-chlorophenyl)-1,3,4-oxadiazol-2(3H)-one, m.p. 92°–95° C.; IR spectrum: 1790 cm$^{-1}$; mass spectrum: 324(12), 280(10), 125(100).

EXAMPLE 3

2.3 ml (19 mmol) of trichloromethyl chloroformate are added dropwise at 10°–20° C. to a mixture of 5.34 g (16 mmol) of 2,6-difluoro-N'-(o-bromophenyl)-benzhydrazide and 5.50 ml (40 mmol) of triethylamine in 35 ml of dioxan. The reaction mixture is heated at the reflux temperature for a further 3 hours and the solvent and excess reagent are subsequently distilled off under reduced pressure. The residue is taken up in diethyl ether and the solution is washed in each case once with water and sodium bicarbonate solution, dried over anhydrous sodium sulfate and evaporated under reduced pressure. After crystallization of the residue from acetone/n-hexane there is obtained pure 3-(2-bromophenyl)-5-(2,6-difluorophenyl)-1,3,4-oxadiazol-2(3H)-one, m.p. 111°–114° C.; IR spectrum: 1790 cm$^{-1}$; mass spectrum: 354/352(15), 310/308(7), 171/169(41), 90(100).

EXAMPLE 4

1.8 ml (19 mmol) of ethyl chloroformate are added dropwise while cooling to a mixture of 4.28 g (14 mmol) of 2-chloro-N'-(α,α,α-trifluoro-o-tolyl)-benzhydrazide and 2.7 ml (19 mmol) of triethylamine in 30 ml of toluene. The reaction mixture is heated at the reflux temperature for a further 4 hours and then extracted with diethyl ether against water and sodium bicarbonate solution. The organic phase is dried over anhydrous magnesium sulfate and evaporated under reduced pressure. The residual oil is then purified by chromatography using ethyl acetate/n-hexane (1:4) as the eluent. In this manner there is obtained ethyl 3-(2-chlorobenzoyl)-2-(α,α,α-trifluoro-o-tolyl)-carbazate as an almost colourless oil, IR spectrum (CHCl$_3$): 3405, 1735, 1710 cm$^{-1}$; $^1$H-NMR (CDCl$_3$): 4.28 (q,OCH$_2$CH$_3$).

The above product is heated at 180° C. by means of an oil-bath for about 16 hours with the addition of 0.14 g (1.1 mmol) of 4-dimethylaminopyridine. After cooling the reaction mixture is taken up in diethyl ether and the solution is washed in each case once with dilute aqueous hydrochloric acid solution and aqueous sodium bicarbonate solution, dried over anhydrous magnesium sulfate and concentrated under reduced pressure. The product is precipitated by adding n-hexane and there is obtained in this manner 5-(2-chlorophenyl)-3-(α,α,α-trifluoro-o-tolyl)-1,3,4-oxadiazol-2(3H)-one, m.p. 100°-102° C.; IR spectrum: 1792 cm$^{-1}$; mass spectrum: 340(39), 296(27), 159(100).

EXAMPLES 5–25

The corresponding benzhydrazides of formula II are reacted with phosgene, trichloromethyl chloroformate or ethyl chloroformate analogously to the procedure described in Examples 1, 2, 3 or 4 in order to manufacture the compounds of formula I in which Y signifies oxygen which are listed in Table 1 hereinafter.

TABLE 1

| Example | R$^1$ | R$^2$ | X | Physical data |
|---|---|---|---|---|
| 5 | 2-Chlorophenyl | 2-Chlorophenyl | O | M.p. 113–114° C.; IR spectrum: 1788 cm$^{-1}$; mass spectrum: 306(20), 262(13), 125(100). |
| 6 | 2-Methoxyphenyl | 2-Chloro-6-fluorophenyl | O | M.p. 109–110° C.; IR spectrum: 1788 cm$^{-1}$; mass spectrum: 320(17), 276(4), 120(100). |
| 7 | α,α,α-Trifluoro-m-tolyl | 2,6-Difluorophenyl | O | M.p. 84.5–85.5° C.; IR spectrum: 1784 cm$^{-1}$; mass spectrum: 342(41), 298(23), 159(100). |
| 8 | α,α,α-Trifluoro-m-tolyl | 2,6-Dimethoxyphenyl | O | M.p. 133–134° C.; IR spectrum: 1776 cm$^{-1}$; mass spectrum: 366(86), 322(69), 163(100), 159(47). |
| 9 | 2-Chlorophenyl | α,α,α-Trifluoro-o-tolyl | O | M.p. 98–100° C.; IR spectrum: 1794 cm$^{-1}$; mass spectrum: 340(15), 296(11), 125(100). |
| 10 | α,α,α-Trifluoro-o-tolyl | 2,6-Difluorophenyl | O | M.p. 115–117° C.; IR spectrum: 1792 cm$^{-1}$; mass spectrum: 342(44), 298(31), 159(100). |
| 11 | 2-Chlorophenyl | " | O | M.p. 113–115° C.; IR spectrum: 1792 cm$^{-1}$; mass spectrum: 308(24), 264(13), 125(100). |
| 12 | " | 2,6-Dichlorophenyl | O | M.p. 94–95° C.; IR spectrum: 1790 cm$^{-1}$; mass spectrum: 340(9), 296(5), 125(100). |
| 13 | " | 2-Chloro-4-fluorophenyl | O | M.p. 126–128° C.; IR spectrum: 1790 cm$^{-1}$; mass spectrum: 324(14), 280(9), 125(100). |
| 14 | 3-Chloro-o-tolyl | 2-Chloro-6-fluorophenyl | O | M.p. 164–165.5° C.; IR spectrum: 1788 cm$^{-1}$; mass spectrum: 338(34), 294(12), 139(100). |
| 15 | 2-Chlorophenyl | 2-Chloro-6-fluorophenyl | S | M.p. 128–130° C.; IR spectrum: 1692, 1688 cm$^{-1}$; mass spectrum: 340(12), 280(23), 125(100). |
| 16 | 3-Chloro-5-trifluoromethyl-2-pyridyl | 2,6-Difluorophenyl | O | M.p. 106–108° C. |
| 17 | 3-Chloro-5-trifluoromethyl-2-pyridyl | 2-Chlorophenyl | O | M.p. 72–75° C. |
| 18 | α,α,α-Trifluor-o-tolyl | 2,6-Difluorophenyl | S | M.p. 117–119° C.; IR spectrum: 1700, 1676 cm$^{-1}$, mass spectrum: 358(40), 298(59), 159(100). |
| 19 | 4-Chloro-2-trifluoromethyl-phenyl | " | O | M.p. 111–113° C.; IR spectrum: 1792 cm$^{-1}$; mass spectrum: 376(18), 332(15), 193(100). |
| 20 | 4-Trifluoromethoxyphenyl | " | O | M.p. 76–78° C.; IR spectrum: 1782 cm$^{-1}$; Mass spectrum: 358(25), 314(6), 175(100). |
| 21 | α,α,α-Trifluoro-o-tolyl | 2-Chlor-4-fluorophenyl | O | Smp. 107–109° C.; IR-Spektrum: 1790 cm$^{-1}$; mass spectrum: 358(35), 314(19), 159(100). |
| 22 | 2-Chloro-4-trifluoromethyl-phenyl | 2,6-Difluorophenyl | O | M.p. 118–120° C.; IR spectrum: 1790 cm$^{-1}$; mass spectrum: 376(20), 332(23), 193(100). |
| 23 | 2-Methylthio-5-trifluoromethyl-phenyl | 2,6-Difluorophenyl | O | M.p. 127–120° c.; IR spectrum: 1790- cm$^{-1}$; mass spectrum: 388(40), 344(3), 204(100). |

TABLE 1-continued

| Example | R$^1$ | R$^2$ | X | Physical data |
|---|---|---|---|---|
| 24 | 2,3-Dimethylphenyl | 2,6-Difluorophenyl | O | M.p. 138-140° C.; IR spectrum: 1788 cm$^{-1}$; mass spectrum: 302(49), 258(5), 118(100). |
| 25 | 2-Fluorophenyl | 2-Chloro-6-fluorophenyl | O | M.p. 111-112° C.; IR spectrum: 1788 cm$^{-1}$; mass spectrum: 308(15), 264(8), 109(100). |

EXAMPLE 26

4.79 g (15 mmol) of 2,6-difluoro-N'-(α,α,α-trifluoro-o-tolyl)-benzhydrazide in 30 ml of toluene are treated with 1.98 g (17 mmol) of thiophosgene and the reaction mixture is heated at the reflux temperature for 5 hours. 4.8 ml (35 mmol) of triethylamine are then added dropwise at 45° C. while cooling and, after cooling, the mixture is stirred at room temperature for about 1 hour. The mixture is subsequently taken up in 100 ml of tert-.butyl methyl ether and the solution is washed in each case once with dilute, ice-cold sodium hydroxide solution and saturated sodium chloride solution, dried over anhydrous magnesium sulfate and evaporated under reduced pressure. The residue is purified by chromatography using acetone/n-hexane (1:4) as the eluent and crystallized from diisopropyl ether/n-hexane. In this manner there is obtained 5-(2,6-difluorophenyl)-3-(α,α,α-trifluoro-o-tolyl)-1,3,4-oxadiazole-2(3H) -thione as a white crystallizate, m.p. 128°-130° C.; mass spectrum: 358(58), 298(15), 289(17), 159(100).

EXAMPLE 27

A mixture of 3.75 g (11.0 mmol) of 5-(2,6-difluorophenyl)-2-(α,α,α-trifluoro-o-tolyl)-2,4-dihydro-3H-1,2,4-triazol-3-one, 1.05 g (11.0 mmol) of dimethyl sulfate and 3.04 g (22.0 mmol) of potassium carbonate in acetone is stirred at the reflux temperature for 16 hours. The insoluble constituents are then filtered off and the evaporated residue is subjected to chromatography on silica gel using ethyl acetate/n-hexane (1:4) as the eluent. As the first fraction there is isolated the apolar secondary component 3-(2,6-difluorophenyl)-5-methoxy-1-(α,α,α-trifluoro-o-tolyl)-1H-1,2,4-triazole, m.p. 118°-119° C.; mass spectrum: 355(75), 298(39), 159(100); $^1$H-NMR (CDCl$_3$): 4.13 (s, OCH$_3$). After further elution with ethyl acetate/n-hexane (2:3) and subsequent recrystallization from diethyl ether/n-hexane there is obtained pure 5-(2,6-difluorophenyl)-4-methyl-2-(α,α,α-trifluoro-o-tolyl)-2,4-dihydro-3H-1,2,4-triazol-3-one, m.p. 98°-99° C., IR spectrum: 1708 cm$^{-1}$; mass spectrum: 355(75), 298(32), 159(100); $^1$H-NMR (CDCl$_3$): 3.30 (s,N-CH$_3$).

EXAMPLES 28-31

The corresponding 2,4-dihydro-3H-1,2,4-triazol-3-ones of formula III are alkylated analogously to the procedure described in Example 27 in order to manufacture the compounds of formula I in which X signifies NR$^3$ and Y signifies oxygen which are listed in Table 2 hereinafter. The corresponding O-alkylated byproducts "(O—R$^3$)" are also indicated.

TABLE 2

| Example | R$^1$ | R$^2$ | R$^3$ | Physical data |
|---|---|---|---|---|
| 28 | 2-Chlorophenyl | 2-Chlorophenyl | Methyl (N—R$^3$) | M.p. 143-145° C.; IR spectrum: 1712 cm$^{-1}$; $^1$H-NMR(CDCl$_3$): 3,30 (s,N—CH$_3$). |
| 29 | " | " | 2-Propynyl (N—R$^3$) | M.p. 82-84° C.; IR spectrum: 3305, 1718 cm$^{-1}$; $^1$H-NMR(CDCl$_3$): 2,21 (t,J = 2.5 Hz,CH), 4.48 (d,J = 2.5 Hz, N—CH$_2$). |
| 29a | " | " | 2-Propynyl (O—R$^3$) | M.p. 92-94° C.; $^1$H-NMR(CDCl$_3$): 2.58 (t,J = 2.5 Hz,CH), 5.16 (d,J = 2.5 Hz, OCH$_2$). |
| 30 | " | 2-Chloro-6-fluorophenyl | Methyl (N—R$^3$) | M.p. 132-134° C.; IR spectrum: 1710 cm$^{-1}$; $^1$H-NMR(CDCl$_3$): 3.24 (s,N—CHH$_3$); mass spektrum: 337(35), 302(91), 125(100). |
| 30a | " | 2-Chloro-6-fluorophenyl | Methyl (O—R$^3$) | M.p. 111-112° C.; mass spectrum: 337(45), 302(11), 280(11), 125(100). |
| 31 | α,α,α-Trifluoro-o-tolyl | 2,6-Difluorophenyl | 2-Propynyl (N—R$^3$) | M.p. 145° C.; $^1$H-NMR(CDCl$_3$):2.17 (t,J = 2.5 Hz, CH), 4.53 (d,J = 2.5 Hz, OCH$_2$). |

EXAMPLE 32

A mixture of 3.25 g (10 mmol) of 5-(2-chloro-6-fluorophenyl)-3-(2-chlorophenyl)-1,3,4-oxadiazol-2(3H)-one (see Example 2) and 2.21 g (5.5 mmol) of 2,4-bis-(4-methoxyphenyl)-1,2-dithioxo-1,3,2,4-dithiaphosphetane (Lawesson reagent) in 50 ml of toluene is heated at reflux temperature for 48 hours. The precipitated product is filtered off and purified by chromatography on silica gel with ethyl acetate/n-hexane (1:4) as the eluent. After subsequent crystallization from acetone/n-hexane there is obtained pure 5-(2-chloro-6-fluorophenyl)-3-(2-chlorophenyl)-1,3,4-oxadiazole-2(3H)-thione, m.p. 112°-114° C.; mass spectrum: 340(5), 305(70), 150(100), 125(49).

EXAMPLE 33

Analogously to the procedure described in Example 32, by treating 5-(2-chloro-6-fluorophenyl)-3-(2-chlorophenyl)-1,3,4-thiadiazol-2(3H)-one (see Example 15) with Lawesson reagent there is manufactured 5-(2-chloro-6-fluorophenyl)-3-(2-chlorophenyl)-1,3,4-thiadiazole-2(3H)-thione, m.p. 126°-128° C.; mass spectrum: 356(2), 321(100), 280(8), 166(59), 125(69).

II. Production of the starting materials of formula II:

EXAMPLE 34

The 2-chloro-6-fluoro-N'-(o-chlorophenyl)-benzhydrazide required as the starting material in Example 2 can be produced as follows:

56.9 g (0.29 mol) of 2-chloro-6-fluorobenzoyl chloride are introduced dropwise into a solution, cooled to 0° C., of 52.8 g (0.29 mol) of 2-chlorophenylhydrazine hydrochloride in 290 ml of pyridine so that the temperature of the solution does not exceed 5° C. The solution is stirred at room temperature for 16 hours and the solvent is subsequently evaporated off azeotropically with toluene under reduced pressure. The resulting red-brown suspension is taken up in 350 ml of diethyl ether and the solution is washed in sequence twice with dilute hydrochloric acid and in each case once with 5% sodium bicarbonate solution and with saturated sodium chloride solution. The aqueous phases are back-extracted with 350 ml of diethyl ether and the combined organic phases are dried over anhydrous magnesium sulfate and then evaporated. After recrystallization of the residue from acetone/n-hexane there is obtained 2-chloro-6-fluoro-N'-(o-chlorophenyl)-benzhydrazide, m.p. 156°-158° C.; IR spectrum: 1692 cm$^{-1}$.

EXAMPLE 35

The 2,6-difluoro-N'-($\alpha,\alpha,\alpha$-trifluoro-o-tolyl)-benzhydrazide required as the starting material in Examples 10 and 26 can be produced as follows:

59.8 g (0.28 mol) of o-trifluoromethyl-phenylhydrazine hydrochloride are placed in a two-phase system of 280 ml of ethyl acetate and 85 ml of water and the mixture is treated portionwise with 84.9 g (0.62 mol) of potassium carbonate while stirring well at 10°-20° C. After a clear solution has formed (15 minutes) there are added dropwise in the next 30 minutes 49.4 g (0.28 mol) of 2,6-difluorobenzoyl chloride so that the temperature is held at a maximum of 25° C. After a further 30 minutes the mixture is diluted with 300 ml of water and the organic phase is separated, washed once with saturated sodium chloride solution, dried over anhydrous sodium sulfate and evaporated to dryness. The residue is dissolved in 30 ml of hot acetone and the 2,6-difluoro-N'-($\alpha,\alpha,\alpha$-trifluoro-o-tolyl)-benzhydrazide is precipitated by adding 500 ml of n-hexane. M.p. 123°-125° C.; IR spectrum: 3405, 1694 cm$^{-1}$.

EXAMPLE 36

The 2,6-difluoro-N'-($\alpha,\alpha,\alpha$-trifluoro-o-tolyl)-benzhydrazide can also be produced as follows:

13.6 g (98 mmol) of potassium carbonate in 70 ml of water are added at 10° C. while stirring to a suspension of 10.4 g (49 mmol) of $\alpha,\alpha,\alpha$-trifluoro-o-tolylhydrazine hydrochloride in 50 ml of ethyl acetate. 7.8 g (49 mmol) of 2,6-difluorobenzoyl fluoride are subsequently added dropwise to the clear solution while cooling so that the internal temperature is maintained at 3° C. The mixture is stirred at 5° C. for 60 minutes and thereafter at 25° C. for 4 hours, and the organic phase is separated. The aqueous phase is back-extracted with 50 ml of ethyl acetate and subsequently treated with 1.85 g (25 mmol) of calcium hydroxide in order to precipitate the calcium fluoride. The combined organic phases are washed in each case once with dilute hydrochloric acid and sodium bicarbonate solution, dried over anhydrous magnesium sulfate and evaporated under reduced pressure. After recrystallization from acetone and n-hexane there is obtained 2,6-difluoro-N'-($\alpha,\alpha,\alpha$-trifluoro-o-tolyl)-benzhydrazide as a white crystallizate, m.p. 129°-130° C.; mass spectrum m/e: M+ 316(26), 141(100).

EXAMPLES 37-57

The corresponding hydrazine of formula V in the form of the hydrochloride is reacted with the corresponding substituted benzoyl chloride or benzoyl fluoride of formula VI analogously to the procedure described in Example 34 or 35 in order to produce the hydrazides of formula II in which X' signifies oxygen which are listed in Table 3 hereinafter. The respective end products of formula I are also identified by the Example number.

TABLE 3

| Example | Example No. of the end product of formula I | R$^1$ | R$^2$ | Physical data |
|---|---|---|---|---|
| 37 | 1 | $\alpha,\alpha,\alpha$-Trifluoro-o-tolyl | 2-Chloro-6-fluorophenyl | M.p. 148-149° C. |
| 38 | 3 | 2-Bromophenyl | 2,6-Difluorophenyl | M.p. 178-180° C. |
| 39 | 4 | $\alpha,\alpha,\alpha$-Trifluoro-o-tolyl | 2-Chlorophenyl | M.p. 119-121° C. |
| 40 | 5 | 2-Chlorophenyl | 2-Chlorophenyl | M.p. 131-132° C. |
| 41 | 6 | 2-Methoxyphenyl | 2-Chloro-6-fluorophenyl | M.p. 138-139° C. |
| 42 | 7 | $\alpha,\alpha,\alpha$-Trifluoro-m-tolyl | 2,6-Difluorophenyl | M.p. 150-151° C. |
| 43 | 8 | $\alpha,\alpha,\alpha$-Trifluro-m-tolyl | 2,6-Dimethoxyphenyl | M.p. 155-156° C. |
| 44 | 9 | 2-Chlorphenyl | $\alpha,\alpha,\alpha$-Trifluoro-o-tolyl | M.p. 174-175° C. |
| 45 | 11 | " | 2,6-Difluorophenyl | M.p. 177-178° C. |
| 46 | 12 | " | 2,6-Dichlorphenyl | Solid (not purified) |
| 47 | 13 | " | 2-Chloro-4-fluoro phenyl | M.p. 122-125° C. |
| 48 | 14 | 3-Chloro-o-tolyl | 2-Chloro-6-fluorophenyl | M.p. 155-157° C. |
| 49 | 16 | 3-Chloro-5-trifluoromethyl-2-pyridyl | 2,6-Difluorophenyl | Solid (not purified) |
| 50 | 17 | 3-Chloro-5-trifluoromethyl-2-pyridyl | 2-Chlorophenyl | Solid (not purified) |
| 51 | 19 | 4-Chloro-2-trifluoromethyl-phenyl | 2,6-Difluorophenyl | M.p. 136-138° C. |
| 52 | 20 | 4-Trifluoromethyoxyphenyl | " | M.p. 159-161° C. |
| 53 | 21 | $\alpha,\alpha,\alpha$-Tri- | 2-Chloro-4-fluoro- | M.p. 114-116° C. |

TABLE 3-continued

| Example | Example No. of the end product of formula I | R¹ | R² | Physical data |
|---|---|---|---|---|
| | | fluoro-o-tolyl | phenyl | |
| 54 | 22 | 2-Chloro-4-tri-fluoromethyl-phenyl | 2,6-Difluorophenyl | M.p. 196–197° C. |
| 55 | 23 | 2-Methylthio-5-trifluoromethyl-phenyl | " | M.p. 148–150° C. |
| 56 | 24 | 2,3-Dimethylphenyl | " | M.p. 154–155° C. |
| 57 | 25 | 2-Fluorophenyl | 2-Chloro-6-fluorophenyl | Smp. 116–118° C. |

EXAMPLE 58

The 2-chloro-6-fluoro-N'-(o-chlorophenyl)-thiobenzhydrazide required as the starting material in Example 15 can be produced as follows:

9.0 g (30 mmol) of 2-chloro-6-fluoro-N'-(o-chlorophenyl)-benzhydrazide (see Example 34) are heated to reflux temperature for 24 hours in 150 ml of toluene together with 6.4 g (15.8 mmol) of Lawesson reagent. The reaction mixture is then subjected to column chromatography on silica gel using ethyl acetate/n-hexane (1:4) as the eluent. The first fraction gives a crystalline mass, the IR spectrum of which exhibits no carbonyl signal. This is subjected to a second chromatography with methylene chloride/n-hexane (13:7) and the evaporated fraction is recrystallized from acetone/n-hexane. There is thus obtained pure 2-chloro-6-fluoro-N'-(o-chlorophenyl)-thiobenzhydrazide as a yellowish crystallizate, m.p. 131°–133° C.; microanalysis:

| | C % | H % | Cl % | F % | N % | S % |
|---|---|---|---|---|---|---|
| Calculated: | 49.54 | 2.88 | 22.50 | 6.03 | 8.89 | 10.17 |
| Found: | 49.51 | 2.93 | 22.58 | 5.64 | 8.86 | 10.37 |

EXAMPLE 59

Analogously to the procedure described in Example 58, by treating 2,6-difluoro-N'-($\alpha,\alpha,\alpha$-trifluoro-o-tolyl)-benzhydrazide (see Examples 35 and 36) with Lawesson reagent there is produced 2,6-difluoro-N'-($\alpha,\alpha,\alpha$-trifluoro-o-tolyl)-thiobenzhydrazide which is required as the starting material in Example 18.

III. Production of the starting materials of formula III:

EXAMPLE 60

The 5-(2,6-difluorophenyl)-2-($\alpha,\alpha,\alpha$-trifluoro-o-tolyl)-2,4-dihydro-3H-1,2,4-triazol-3-one required as the starting material in Examples 27 and 31 can be produced as follows:

A mixture of 59.7 g (0.19 mol) of 2,6-difluoro-N'-($\alpha,\alpha,\alpha$-trifluoro-o-tolyl)-benzhydrazide (see Examples 35 and 36) and 31.8 g (0.21 mol) of phosphorus oxychloride is heated at reflux temperature for one hour. The reaction mixture is subsequently taken up in 50 ml of dioxan and the solution, which contains the 2,6-difluoro-N'-($\alpha,\alpha,\alpha$-trifluoro-o-tolyl)-benzhydrazinoyl chloride which is produced in the first reaction step and which is not isolated, is added dropwise to a well-stirred mixture of 340 ml of 25% ammonia solution and 340 ml of dioxan at −4° C. to −6° C. The mixture is then diluted with diethyl ether until phase separation occurs and the ether phase is extracted three times with 2N hydrochloric acid. The acidic aqueous phase is made alkaline (pH greater than 9) with 30% sodium hydroxide solution and thereafter extracted with diethyl ether. After drying the ether phase over anhydrous magnesium sulfate and adding n-hexane there is obtained 2,6-difluoro-N'-($\alpha,\alpha,\alpha$-trifluoro-o-toluidino)-benzamidrazone as a yellowish, crystalline precipitate, m.p. 108.5°–109.5° C.

10 g (32 mmol) of the above intermediate and 4.8 ml (35 mmol) of triethylamine in 60 ml of toluene are treated at 0° C. while stirring with a 1:1 solution of 6.0 ml (63 mmol) of ethyl chloroformate and toluene. The mixture is stirred firstly at room temperature for one hour and then heated at reflux temperature for about 16 hours. The cooled reaction mixture is filtered off and washed with diethyl ether. In order to remove triethylammonium hydrochloride, the mixture is washed well with water and the insoluble residue is dried at 80° C./100 mmHg. In this manner there is obtained 5-(2,6-difluorophenyl)-2-($\alpha,\alpha,\alpha$-trifluoro-o-tolyl)-2,4-dihydro-3H-1,2,4-triazol-3-one, m.p. 259°–260° C.

EXAMPLE 61

The 5-(2,6-difluorophenyl)-2-($\alpha,\alpha,\alpha$-trifluoro-o-tolyl)-2,4-dihydro-3H-1,2,4-triazol-3-one can also be produced as follows:

15.8 g (50 mmol) of 2,6-difluoro-N'-($\alpha,\alpha,\alpha$-trifluoro-o-tolyl)-benzhydrazide (see Examples 35 and 36) are suspended in 50 ml of toluene and the suspension is heated at 100° C. for 5 hours together with 8.0 g (52 mmol) of phosphorus oxychloride. Thereafter, the mixture is diluted with 150 ml of toluene and treated with 100 ml of water while stirring well at 5° C. The organic phase is separated, washed with semi-saturated sodium chloride solution, dried over anhydrous magnesium sulfate and evaporated under reduced pressure. 15.9 g of 2,6-difluoro-N'-($\alpha,\alpha,\alpha$-trifluro-o-tolyl)-benzhydrazinoyl chloride are obtained as an oil, mass spectrum: 334(56), 298(33), 159(100).

15 g (45 mmol) of the above intermediate are dissolved in 90 ml of acetone and treated with a solution of 5.9 g (90 mmol) of sodium cyanate in 10 ml of water. The reaction mixture is heated at the reflux temperature for 20 minutes, then diluted with 270 ml of water and left to cool while stirring. The resulting crystals are filtered off, washed with diethyl ether and dried at 60° C. under reduced pressure. Pure 5-(2,6-difluorophenyl)-2-($\alpha,\alpha,\alpha$-trifluoro-o-tolyl)-2,4-dihydro-3H-1,2,4-triazol-3-one is obtained as a white crystallizate, m.p. 273°–274° C.

EXAMPLES 62 AND 63

Analogously to the procedure described in Examples 60 and 61, the corresponding benzhydrazide of formula II' is treated with phosphorus oxychloride and the resulting benzhydrazinoyl chloride of formula VII is either subjected to an aminolysis with ammonia and the product of the aminolysis, i.e. the corresponding amidrazone of formula XII or an acid addition salt thereof, is treated with ethyl chloroformate, or is reacted with an alkali cyanate in order to produce the starting materials of formula III which are listed in Table 4 hereinafter. The respective end products of formula I are also identified by their Example number.

TABLE 4

| Example | Example No. of the end product of formula I | R¹ | R² | Physical data |
|---|---|---|---|---|
| 62 | 28, 29 | 2-Chlorophenyl | 2-Chlorophenyl | M.p. 231° C. |
| 63 | 30 | 2-Chlorophenyl | 2-Chloro-6-fluorophenyl | M.p. 223–224° C. |

The respective amidrazones of formula XII are 2-chloro-N'-(o-chlorophenyl)-benzamidrazone, m.p. 139°–140.5° C., and 2-chloro-6-fluoro-N'-(o-chlorophenyl)-benzamidrazone, m.p. 162°–163° C.

IV. Formulation Examples:

EXAMPLE 64

An emulsifiable concentrate has the following composition:

|  | g/liter |
|---|---|
| Compound of formula I (active substance) | 250 |
| N-Methyl-2-pyrrolidone (solvent) | 400 |
| Arkopal N100 ® (nonylphenol polyglycol ether; non-ionic tenside) | 75 |
| Phenylsulfonate CAL ® (calcium dodecylbenzenesulfonate; anionic tenside) | 25 |
| Solvesso 100 ® (solvent containing more than 95 vol. % aromatics) | ad 1 liter |

The active substance and the tensides are dissolved in the solvents. After dilution with water the thus-obtained emulsifiable concentrate gives and emulsion which is well-suited as a spray liquor.

EXAMPLE 65

A spray powder has the following composition:

|  | Weight percent |
|---|---|
| Compound of formula I (active substance) | 50 |
| Sodium lauryl sulfate (wetting/dispersing agent) | 1 |
| Sodium lignosulfonate (dispersing agent) | 2 |
| Hydrated silicic acid (about 87% SiO₂) (inert pulverous carrier substances | 5 |
| Kaolin (mainly Al₂(Si₂O₅)(OH)₄) | 42 |
|  | 100 |

The active substance is mixed homogeneously with the remaining formulation components in a suitable apparatus. The resulting powder is then finely ground in a suitable milling aggregate (e.g. pin, hammer, ball or air-jet mill) to a particle size which is required for an optimal biological activity and thereafter again mixed. The so-produced spray powder is spontaneously wetted with water and gives well-suspended, ready-for-use spray liquors.

I claim:

1. Compounds of the formula

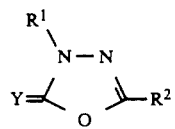

wherein
R¹ is phenyl, pyridyl, phenyl substituted with up to 5 substituents selected from the group consisting of halo, $C_{1-4}$ alkyl, halomethyl, $C_{1-3}$-alkoxy, $C_{1-2}$-alkylthio, $C_{1-3}$-haloalkoxy, $C_{1-2}$-haloalkylthio and cyano, of which no more than 4 are halo, 3 are alkyl, 2 are halomethyl or 1 is alkoxy, alkylthio, haloalkoxy, haloalkylthio or cyano, or pyridyl substituted with 1 or 2 halogen atoms, 1 or 2 methyl groups or a halomethyl group;
R² is phenyl substituted with up to 3 substituents selected from the group consisting of halo, methyl, halomethyl and methoxy, of which no more than 2 are methoxy or 1 is methyl or halomethyl, with at least one of the two o-positions being occupied;
Y is oxygen or sulfur; and
R³ is methyl, halomethyl or 2-propynyl.

2. A compound according to claim 1, wherein R¹ is phenyl monosubstituted with fluorine, chlorine, bromine, methyl, trifluoromethyl or halomethoxy, or phenyl disubstituted with fluorine, chlorine, methyl or a combination of two different substituents selected from the group consisting of fluorine, chlorine, bromine, methyl, trifluoromethyl and halomethoxy, with one of the two o-positions being occupied.

3. A compound according to claim 2, wherein R¹ is substituted such that fluorine, chlorine, bromine, methyl or trifluoromethyl is situated in the o-position.

4. A compound according to claim 2, wherein R² is phenyl monosubstituted with fluorine, chlorine or bromine, or phenyl disubstituted with fluorine, chlorine, or a combination of two different substituents selected from the group consisting of fluorine, chlorine and bromine.

5. A compound according to claim 4, wherein R² is 2-chlorophenyl, 2-chloro-4-fluorophenyl, 2-chloro-6-fluorophenyl or 2,6-difluorophenyl.

6. A compound according to claim 1 which is selected from the group consisting of
5-(2-Chloro-6-fluorophenyl)-3-(α,α,α-trifluoro-o-tolyl)-1,3,4-oxadiazol-2(3H)-one,
5-(2-chloro-6-fluorophenyl)-3-(2-chlorophenyl)-1,3,4-oxadiazol-2(3H)-one,
5-(2,6-difluorophenyl)-3-(α,α,α-trifluoro-o-tolyl)-1,3,4-oxadiazol-2(3H)-one,
5-(2-chloro-4-fluorophenyl)-3-(2-chlorophenyl)-1,3,4-oxadiazol-2(3H)-one,
5-(2-chloro-6-fluorophenyl)-3-(3-chloro-o-tolyl)-1,3,4-oxadiazol-2(3H)-one,
5-(2-chloro-6-fluorophenyl)-3-(2-chlorophenyl)-1,3,4-oxadiazole-2(3H)-thione,
3-(2-chlorophenyl)-5-(2,6-difluorophenyl)-1,3,4-oxadiazol-2(3H)-one,
3-(2-chlorophenyl)-5-(2,6-dichlorophenyl)-1,3,4-oxadiazol-2(3H)-one,
5-(2,6-difluorophenyl)-3-(α,α,α-trifluoro-o-tolyl)-1,3,4-oxadiazole-2(3H)-thione and
3-(2-bromophenyl)-5-(2,6-difluorophenyl)-1,3,4-oxadiazol-2(3H)-one.

7. 5-(2-chlorophenyl)-3-(α,α,α-trifluoro-o-tolyl)-1,3,4-oxadiazol-2(3H)-one.

8. 5-(2-chloro-6-fluorophenyl)-3-(2-fluorophenyl)-1,3,4-oxadiazol-2(3H)-one.

9. A composition for the control of insects and mites which contains as an active ingredient an effective amount of a compound in accordance with claim 1 or 2.

* * * * *